United States Patent [19]

Inouye et al.

[11] 4,116,393
[45] Sep. 26, 1978

[54] APPARATUS FOR COLLECTING AND PREPARING SAMPLE YARNS TO BE TESTED

[75] Inventors: Yoshinori Inouye; Hiromitsu Kanamori; Nobuo Tsuchida; Syozo Morishita; Tetsuhiko Endo, all of Ohtsu, Japan

[73] Assignee: Toray Industries, Inc., Tokyo, Japan

[21] Appl. No.: 841,052

[22] Filed: Oct. 11, 1977

[30] Foreign Application Priority Data

Oct. 9, 1976 [JP] Japan .................................. 51/121443

[51] Int. Cl.² ......................... B65H 54/00; G01L 5/04
[52] U.S. Cl. .......................................... 242/1; 73/160;
242/35.6 R; 242/47; 242/47.01
[58] Field of Search ............. 242/1, 47, 35.6 R, 37 A, 242/47.01, 47.12; 73/160; 28/100, 141, 193

[56] References Cited

U.S. PATENT DOCUMENTS

| 3,017,129 | 1/1962 | Trost | 242/35.6 R |
|---|---|---|---|
| 3,377,676 | 4/1968 | Furst | 242/35.6 R X |
| 3,419,225 | 12/1968 | Rosen | 242/47.12 |
| 3,549,299 | 12/1970 | Rosen | 242/47.12 |
| 3,796,386 | 3/1974 | Tannert | 242/47.12 |
| 3,891,155 | 6/1975 | Naegeli | 242/47.01 X |
| 3,944,156 | 3/1976 | Jacobsson et al. | 242/47.12 |
| 3,999,717 | 12/1976 | Jacobsson et al. | 242/47.01 |

FOREIGN PATENT DOCUMENTS 1,120,812 4/1956 France .................................. 242/35.6 R Primary Examiner—Stanley N. Gilreath
Attorney, Agent, or Firm—Armstrong, Nikaido, Marmelstein & Kubovcik

[57] ABSTRACT

A sample yarn-collecting apparatus for preparing a continuous yarn knotted in an end-to-end manner, in which sample yarns having a certain length are collected from a plurality of yarn packages, each of them are connected in succession in an end-to-end manner to obtain one continuous yarn, and the continuous yarn is wound temporarily and thereafter continuously unwound to be fed to testing means while storing it in a quantity within a predetermined range, is disclosed. This apparatus comprises sample yarn collecting means for collecting sample yarns from packages and connecting each of them to form one continuous yarn, means for storing the continuous yarn fed from said collecting means on a rotary member by winding it and feeding the continuous yarn wound and stored on the rotary member to testing means by unwinding it, and supplementary means for controlling the above two means.

24 Claims, 31 Drawing Figures

Fig. 1
Fig. 2
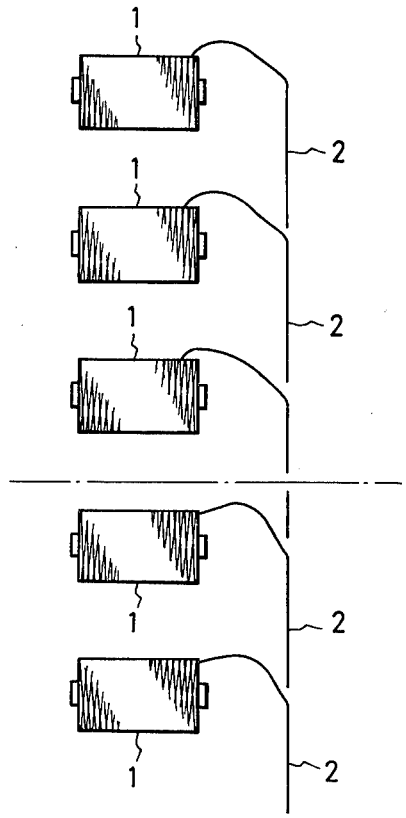
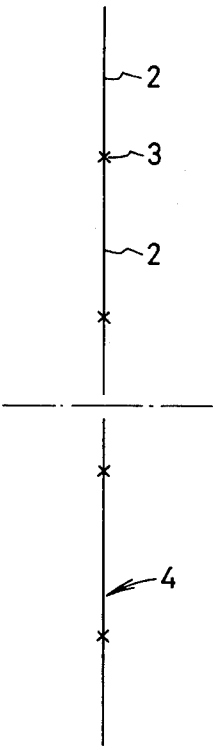
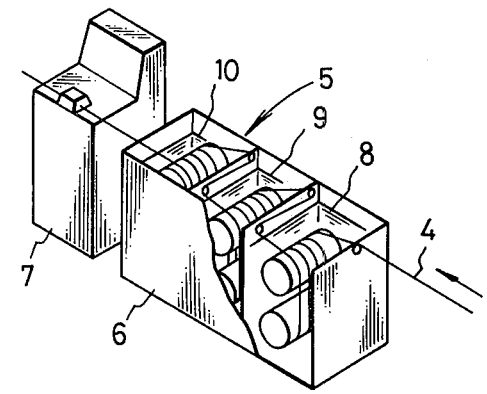
Fig. 3
Fig. 4
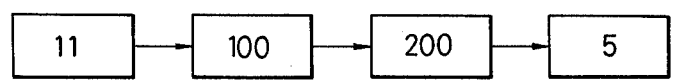

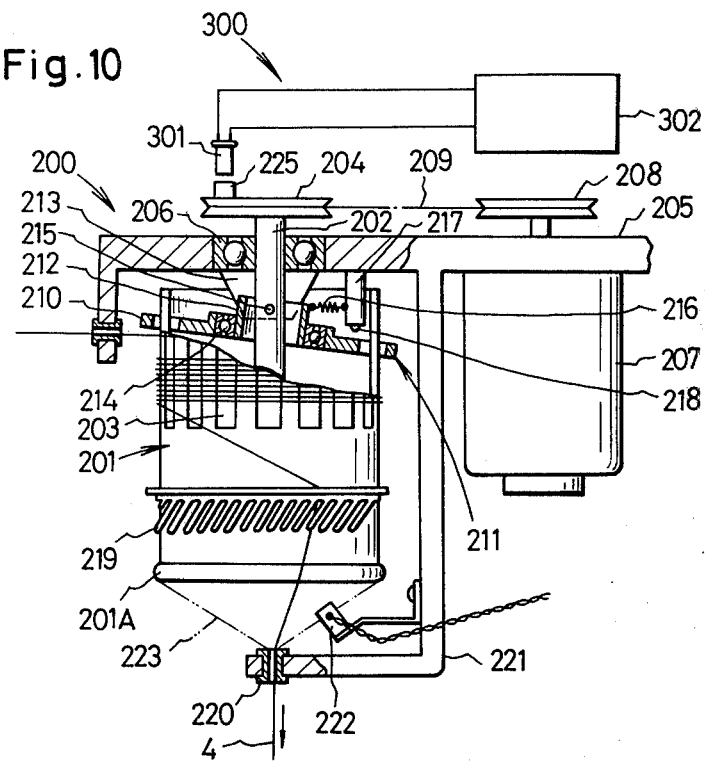
Fig. 10
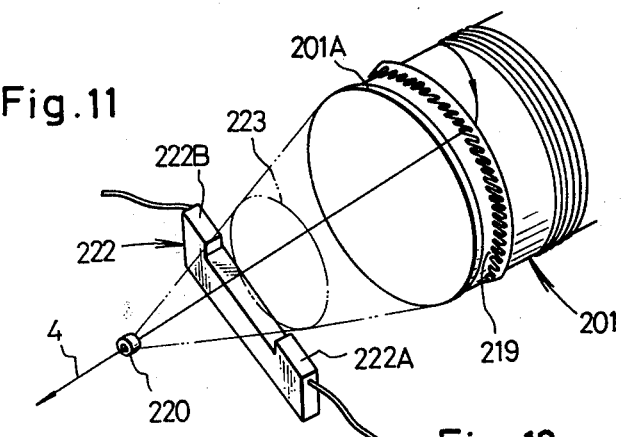
Fig. 11
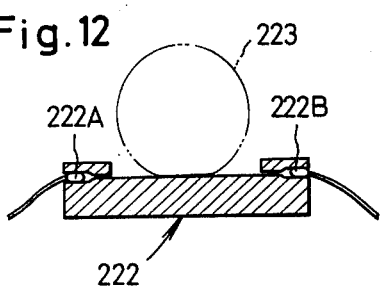
Fig. 12
Fig. 13

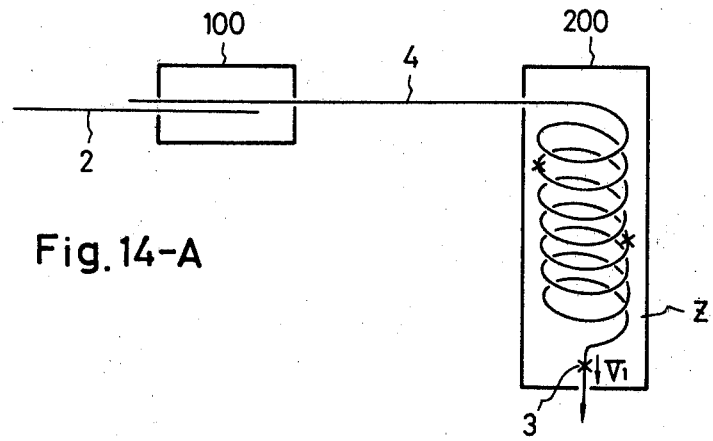
Fig.14-A
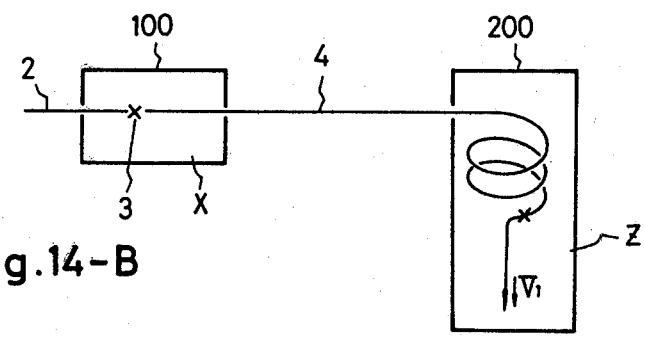
Fig.14-B
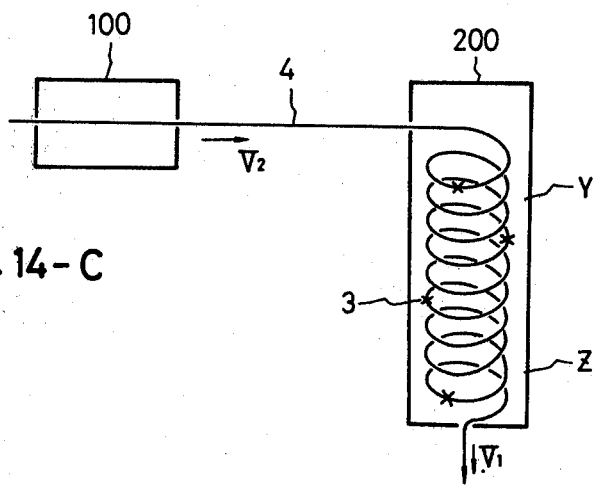
Fig.14-C

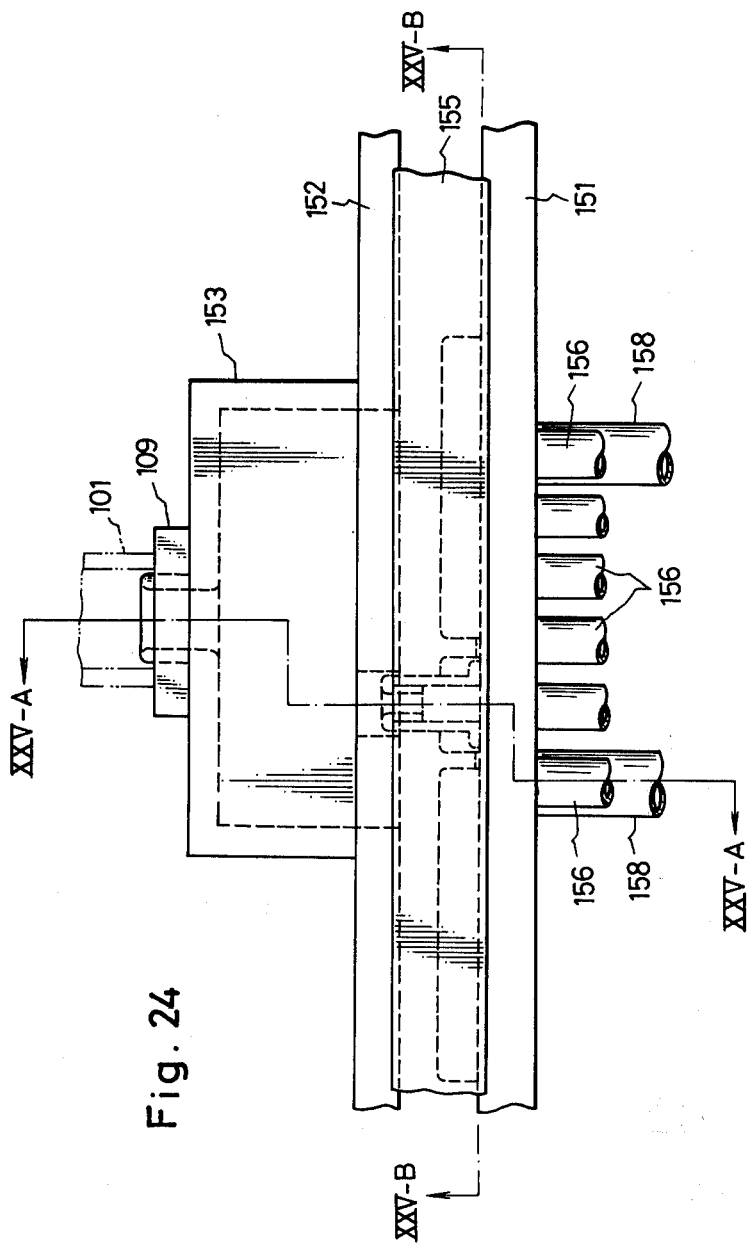

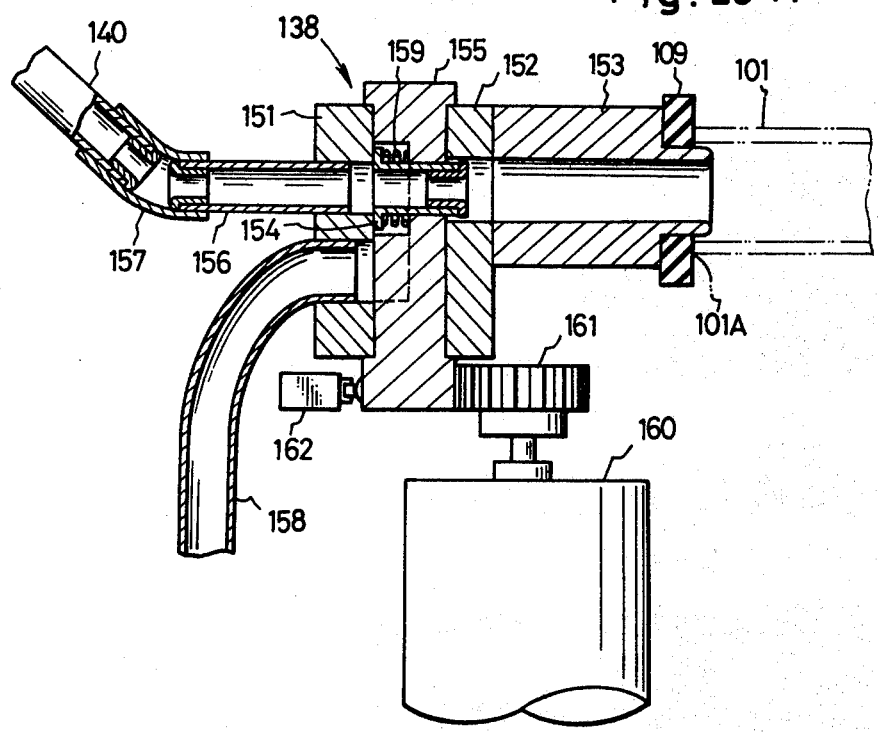
Fig. 25-A

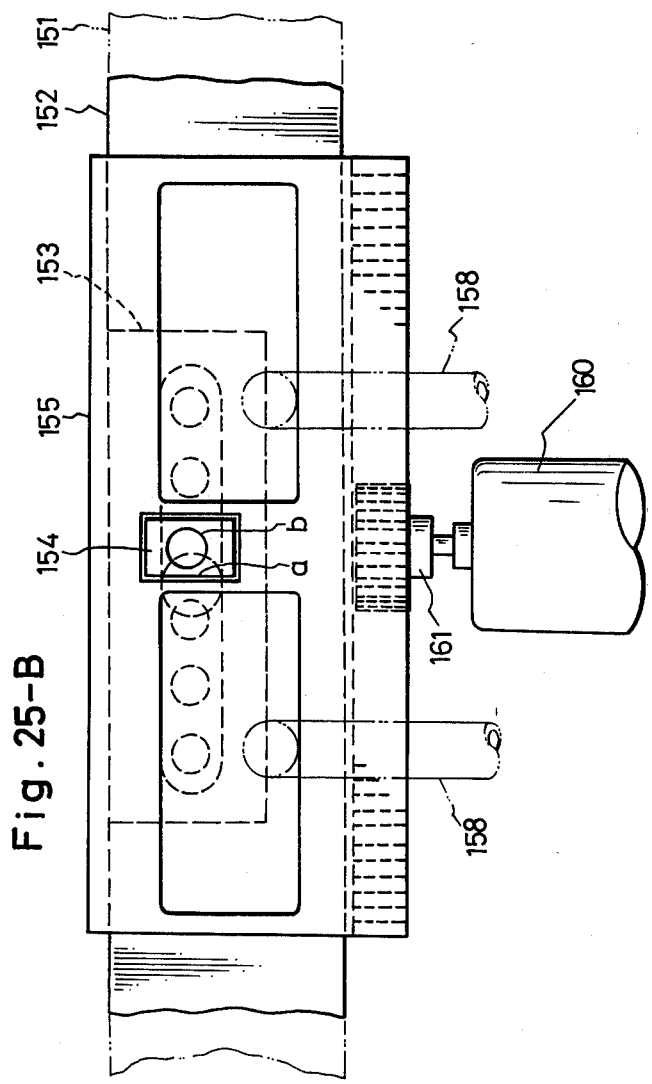

APPARATUS FOR COLLECTING AND PREPARING SAMPLE YARNS TO BE TESTED

BACKGROUND OF THE INVENTION

The present invention relates to a sample yarn-collecting apparatus for preparing a continuous yarn knotted in an end-to-end manner with sample yarns having a certain length from a plurality of packages in order to check the quality and character of the yarns.

In yarn manufacturing plants or spinning plants, sample yarns are collected from surface portions of full wound bobbins and their properties such as strength, elongation, evenness, dyeability and fineness are tested. As means for conducting these tests accurately at high efficiency, there has heretofore been adopted a method in which sample yarns having a certain length are collected from respective packages, these sample yarns are connected to one another in an end-to-end manner to form one continuous yarn and this sample yarn is fed to testing means for the above tests. The principle of this method will now be described by reference to FIGS. 1 and 2. At first, sample yarns 2 having a certain length are taken out and cut from surface portions of many wound bobbins 1, and these sample yarns 2 are connected to one another in an end-to-end manner to form a continuous yarn 4 having many knots 3, as shown in FIG. 2. Then, the continuous yarn 4 is passed through testing means, for example, a dyeability tester 5 shown in FIG. 3. This testing means 5 comprises, for example, a dyeing machine 6 and a measuring and analyzing equipment 7. This dyeing machine includes a scouring zone 8 for scouring a sample yarn, a dyeing zone 9 and a water-washing 10. The continuous yarn 4 is dyed while it passes through these zones 8, 9 and 10 of the dyeing machine 6 in succession, and dyeability characteristics of the respective sample yarns 2 are continuously and relatively determined by the measuring and analyzing equipment 7. If a standard yarn is incorporated in the continuous yarn 4, it will be possible to compare the sample yarn with the standard yarn.

If it is intended to work this method in a continuous manner, it will be necessary to perform continuously in sequence operations of collecting sample yarns having a certain length from respective wound bobbins, connecting the sample yarns to one another in an end-to-end manner to form one continuous yarn and supplying this continuous yarn to testing means, and it will also be necessary to provide an apparatus capable of performing these operations. More specifically, an apparatus having a layout as shown in FIG. 4 must be employed, which apparatus comprises hanging means 11 for supporting a plurality of wound bobbins in the state hung thereon, sample yarn collecting means for collecting sample yarns in succession from said hanging means and connecting the end of each collected sample yarn to the end of the continuous yarn which has been fed to testing means, means 200 for storing the continuous yarn and feeding it to testing means, and testing means 5. This apparatus including a series of the foregoing means requires special elements which are not necessary in other fiber machines treating a continuous yarn at a constant speed in a continuous manner.

In general, it is very difficult to connect two running yarns without stopping them, and practically, the connecting operation is carried out while once stopping the running yarns. Accordingly, also in the above-mentioned apparatus, an element for stopping running of sample yarns for the connecting operation should be included and combined with a series of the foregoing means.

On the other hand, in the testing means, once the continuous yarn is supplied thereto and the test is initiated, the operation of the testing means should not be stopped in the midway. For example, if the above-mentioned dyeing machine is stopped during the test, determined dyeability characteristics of the sample yarn which happened to be dipped in the dyeing zone at the stoppage of the dyeing machine are not reliable and data obtained with respect to this sample yarn cannot be compared with test results of other sample yarns, because the dyeability characteristics vary depending on the time for passage through the dyeing zone.

As is apparent from the foregoing, the above apparatus should include means continuously rotating in a certain direction and means for stopping said rotation in addition to a series of the above-mentioned means. If these additional means are included, the structure, mechanism and operation of the apparatus will be very complicate.

The above apparatus is further required to have an ability to measure lengths of respective yarns precisely and assuredly. In the dyeing machine, the yarn passage from the inlet to the measuring and anylyzing equipment through the dyeing zone is very long, and in general, several or more knots of sample yarns are present along this yarn passage. Accordingly, in order to prevent confusion of the sequence of connection of the sample yarns, it is necessary to discriminate the knotting points assuredly and to prevent knots from getting loose in the dyeing zone or from being entangled with other knots. In view of the foregoing, it will be possible to include knotting means as disclosed in Japanese Patent Application Laid-Open Specifications No. 123964/75 and No. 123965/75 into the above apparatus comprising a series of the above-mentioned means and also include yarn storing means as disclosed in Japanese Patent Publication No. 9865/72 into the above apparatus, and to try to utilize the resulting apparatus for working a method comprising collecting sample yarns having a certain length from many wound bobbins, connecting them to one another in an end-to-end manner to form one continuous yarn and feeding the resulting test yarn continuously to testing means.

However, it has been found that this trial results in the following disadvantages.

(1) The knotting mechanism is complicate, and a long yarn end is left in a package from which a sample yarn has been collected and it is readily entrangled with a yarn end of a package from which a sample yarn is going to be collected. Further, in the combination of the hanging means with packages, troublesome operations such as pick finding are involved and the apparatus system is large and lacks in versatility. Accordingly, this system can hardly be put into practical application.

(2) The testing means still involves various defects. For example, when a trouble takes place, a complete and prompt measure cannot be taken to expel the trouble, and because a number of independent steps are included, test results cannot be obtained promptly. Furthermore, the sequence of sample yarns is readily confused or the sample yarn feeding operation is complicate. When running of test yarn has to be stopped because of yarn breakage or the like trouble in the measuring and analyzing equipment, since a long time has passed from the start of the sampling operation, it is very troublesome and difficult to find out and re-collect samples with respect to all the sample yarns wound on the sample cheese on which the broken sample yarn has been wound. Accordingly, it is impossible to cope with such trouble at a high efficiency. Moreover, since a great number of sample yarns are wound on one sample cheese and the first collected sample yarn is subjected to the test finally, it takes a long time to obtain test results of all the sample yarns on one sample cheese and the sequence of appearance of test results in sample yarns on one sample cheese is reverse to the sampling sequence. Therefore, confusion is readily caused. Furthermore, since feeding of sample cheeses to the testing machine is accomplished through an operator, a trouble or errneous operation is readily caused.

(3) It is necessary to solve a problem how to combine the knotting means with the yarn storing means while allowing them to exert their functions most effectively.

OBJECTS OF THE INVENTION

It is a primary object of the present invention to provide an apparatus for preparing one continuous yarn by collecting sample yarns having a certain length from many packages, respectively, and connecting them to one another in an end-to-end manner.

Another object of the present invention is to provide an apparatus for storing the so prepared continuous yarn and feeding it continuously to test means for testing properties of the respective sample yarns of said continuous yarn.

Still another object of the present invention is to provide an apparatus for collecting sample yarns having a certain length from many packages, respectively, connecting each of the collected sample yarns in an end-to-end manner to a continuous yarn being fed to testing means, and storing the resulting continuous yarn along a certain length while continuously feeding the continuous yarn to the testing means.

A further object of the present invention is to provide an apparatus having a simple structure as the above-mentioned apparatus.

A still further object of the present invention is to provide an apparatus as mentioned above, in which even if a trouble not allowing smooth feeding of the continuous yarn to the testing means takes place, the trouble can be eliminated very simply.

BRIEF SUMMARY OF THE INVENTION

In accordance with the present invention, the foregoing objects and other objects and advantages can be attained by an apparatus for preparing test yarns composed of end-to-end connected sample yarns having a certain length, comprising (1) sample yarn collecting means which collects sample yarns having a certain length from a plurality of yarn packages and connect them to one another in an end-to-end manner to form one continuous yarn, (2) means for storing and feeding said continuous yarns, said storing and feeding means including a storing drum on which the continuous yarn is stored by introducing the continuous yarn from the peripheral direction of said drum and winding a predetermined quantity of the continuous yarn on the drum and from which the stored continuous yarns is continuously taken out from the axial direction of the drum, the speed for winding the continuous yarn on the storing drum being higher than the speed for taking out the continuous yarn from said storing drum, and (3) a preset counter for indicating and counting a predetermined length of the continuous yarn stored in said storing and feeding means by one storing operation, wherein said preset counter transmits a signal when said storing and feeding means completes storing of the predetermined length of the continuous yarn, to instruct said storing and feeding means to stop the yarn storing operation and to instruct said sample yarn collecting means to prepare for the yarn knotting operation, and wherein said sample yarn collecting means transmits a signal on completion of the sample yarn collecting operation and the yarn knotting operation to cause said storing and feeding means to initiate the yarn storing operation.

As the sample yarn collecting means, there is preferably employed an apparatus comprising (1) a yarn introduction guide, the front end of which guides and introduces sample yarns, (2) a suction pipe which is movable so that the inlet of said pipe on the suction side is connected to or separated from the rear end of said yarn introduction guide, (3) a knotter for connecting the rear end of a continuous yarn formed by connecting a plurality of sample yarns to one another in an end-to-end manner, to the end of a fresh sample yarn introduced from said yarn introduction guide, and (4) a yarn feed-out guide for guiding the continuous yarn in which said knotting operation has been completed, wherein when said suction pipe is separated from the rear end of said yarn introduction guide, it sucks and holds both the end of the sample yarn from the yarn introduction guide and the end of said continuous yarn through said yarn feed-out guide.

BRIEF DESCRIPTION OF THE DRAWING

FIGS. 1 and 2 are diagrams illustrating a method for collecting sample yarns from packages;

FIG. 3 is a perspective view illustrating one exmple of means for measuring properties of sample yarns;

FIG. 4 is a view illustrating an arrangement of sample yarn collecting means and storing and feeding means;

FIG. 10 is a diagram illustrating the main part of typical storing and feeding means;

FIG. 11 is a diagram illustrating the state where a continuous yarn is unwound and taken out from a storing drum;

FIGS. 12 and 13 are diagrams illustrating a method for detecting the frequency of occurrence of ballooning;

FIGS. 14-A to 14-C are diagrams illustrating the concept of a method for storing a continuous yarn;

FIG. 24 is a top plan view showing yarn sucking unit;

FIGS. 25-A and 25-B are sectional views taken along the lines XXV-A - XXV-A and XXV-B - XXV-B of FIG. 24, respectively;

DETAILED DESCRIPTION OF THE INVENTION

Figure 5:
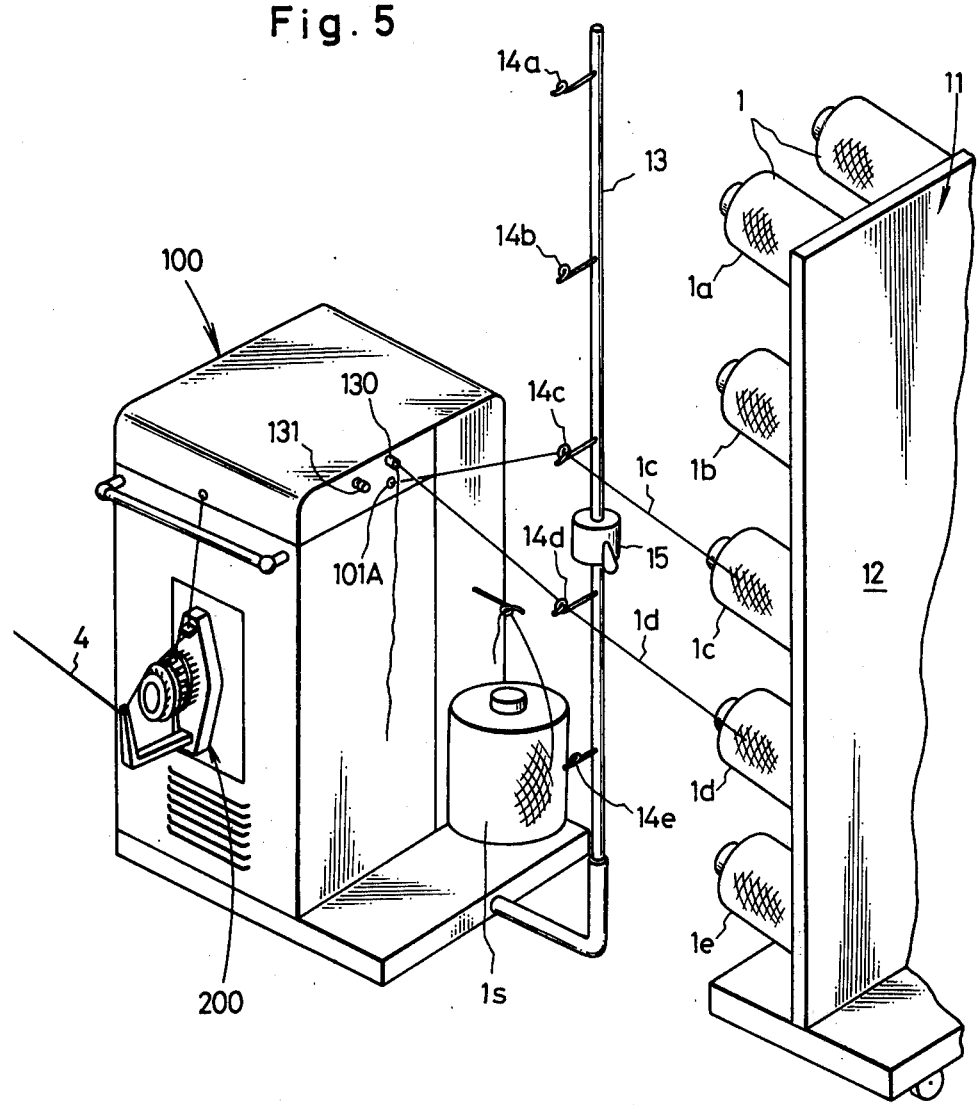
FIG. 5 is a perspective view showing the apparatus of package hanging means, sample yarn collecting means and storing and feeding means in the apparatus of the present invention.

FIG. 4 is a typical flow sheet of the sample yarn testing system in which the apparatus of the present invention is included. The sample yarn testing system of this flow sheet comprises package hanging means 11 on which a plurality of packages are hung, sample yarn collecting mean 100 (hereinafter referred to as collecting means) for collecting sample yarns having a certain length (by the term "sample yarn" is meant a yarn having a certain limited length) from the packages on the hanging means and connecting the end of each sample yarn in an end-to-end manner to the end of a continuous yarn being fed to testing means (by the term "continuous yarn" is meant one continuous yarn composed of sample yarns end-to-end connected to one another) and storing and feeding means 200 for storing said continuous yarn and feeding it to testing means (hereinafter referred to as storing and feeding means), and testing means 5 for testing and determining properties of the yarns of said packages (hereinafter referred to as testing means).

The present invention is to provide specific devices of said sample yarn collecting means 100 and said storing and feeding means 200 in the above flow sheet.

FIG. 5 is a perspective view illustrating one embodiment of the apparatus of the present invention. In this embodiment, sample yarn collecting means 100 and storing and feeding means 200 are contained in one box. In front of this box, there is disposed hanging means 11 including a plurality of packages 1 (1a, 1b, 1c, ...) hung on a stand 12, and a guide stand 13 is disposed between the hanging means 11 and the above-mentioned box. Pig tail guides 14 (14a, 14b, 14c, ...) and a switch 15 for starting or stopping the apparatus of the present invention are mounted on the guide stand 13.

Sample yarn collecting means 100 and storing and feeding means 200 constituting the apparatus of the present invention will now be described in detail.

Collecting Means

Figure 6:
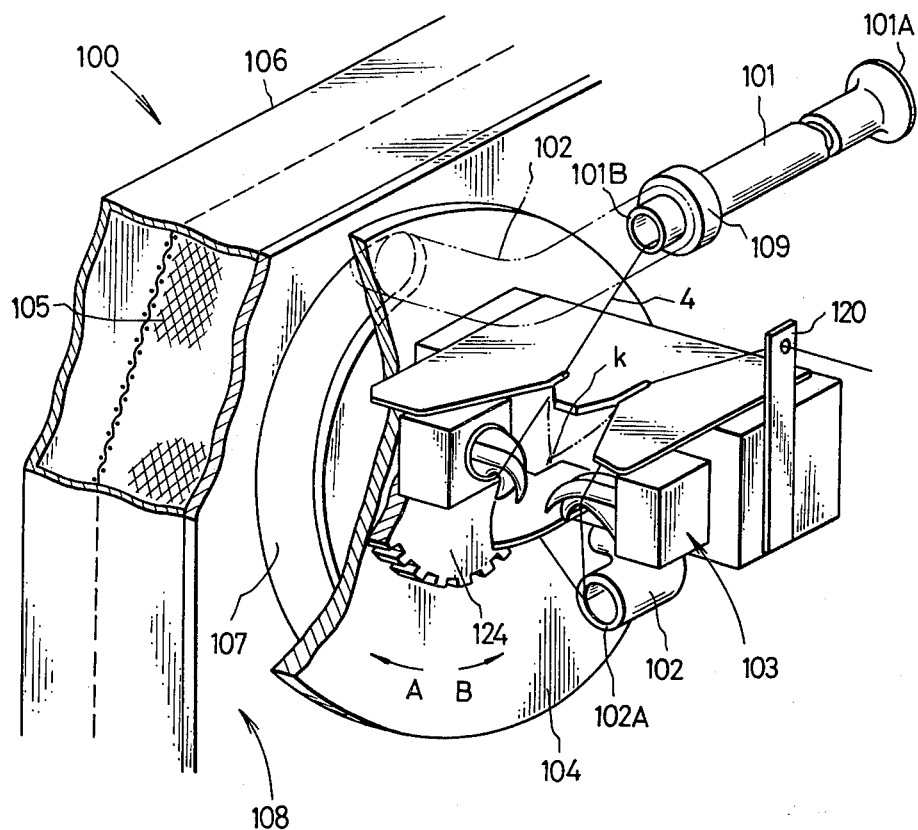
FIG. 6 is a perspective view illustrating the main part of the sample yarn collecting means.

FIG. 6 is a perspective view illustrating the main part of collecting means 100 included in the box shown in FIG. 5. The collecting means 100 comprises as main elements a sample yarn introduction guide 101 (hereinafter referred to as yarn guide), a sample yarn sucking pipe 102 (hereinafter referred to as suction pipe), a yarn knotter 103 and a yarn feed-out guide 120.

The yarn guide 101 is a cylindrical guide, and one end (front end 101A) of the yarn guide 101 is opened toward the guide stand shown in FIG. 5. The other end (rear end 101B) of the yarn guide 101 is attached toward the interior of the collecting means 100. The suction pipe 102 is disposed and arranged so that the rear end 102 thereof is connected to or separated from the rear end 101B of the yarn guide 101. This suction pipe 102 makes the function of sucking the end of a freshly collected sample yarn coming from the yarn guide 101 and the end of a yarn already collected and hung on the feed-out guide 120 simultaneously from the front end 102A thereof to hold these yarn ends, and also the function of bringing said held portions of the sample yarns into the knotter 103 for the knotting operation while the rear end 102A of the suction pipe 102 is being separated from the rear end 101B of the yarn guide 101.

Elements for enabling the foregoing operations in the collecting means 100 will now be described by reference to FIGS. 6 to 8.

A rotary disc 104 having a plane face in the direction to the yarn guide 101 and being capable of rotating within a certain angle is attached to a stand (not shown) for the collecting means 100, and an L-shaped suction pipe 102 is attached to the disc 104. The suction pipe 102 is fixed so that the end 102B thereof pierces through the rotary disc 104 and is opened to the back face thereof. The opening of the end 102B confronts an arcuate groove 107 formed on a waste store chamber 106 and it is communicated with the chamber 6 through said groove 107. When the rotary disc 104 is rotated, the opening of the end 102B is moved along the groove 107. When the suction pipe 102 and rotary disc 104 are rotated clockwise, namely in a direction indicated by an arrow A, the front end 102A of the suction pipe 102 is connected with the rear end 101B of the yarn guide 101 as indicated by chain lines in FIGS. 6 and 8. When the suction pipe 102 and rotary disc 104 are rotated counterclockwise, namely in a direction indicated by an arrow B, the front end 102A of the suction pipe 102 is located below the knotter 103 as indicated by solid lines in FIGS. 6 and 8. The rotary disc 104 is disposed so that the foregoing movements can be given to the suction pipe 102. A net-stretched waste storing chamber 106 is disposed on the back face of the rotary disc 104, namely on the side where the knotter 103 is not present. As shown in FIG. 7, the rear end 102B of the suction pipe 102 is extended into the waste store chamber 106. The above arcuate groove 107 allowing rotation of the rotary disc 104 is formed on the front wall 108 of the waste store chamber 106, and the rear end 102B of the suction pipe 102 is always communicated with the waste store chamber 106 through the groove 107. The waste store chamber 106 is divided into two chambers by a net 105, and the rear chamber is connected to a vacuum generating source (not shown).

When the vacuum generating source is actuated, air is sucked from the front end 102A of the suction pipe 102, and if the front end 102A of the suction pipe 102 is connected to the rear end 101B of the yarn guide 101, air is sucked from the front end 101A of the yarn guide 101. At the connecting part, a seal member 109 is preferably disposed on the rear end 101B or the front end 102A. In order to prevent air from being sucked from the groove 107 through the clearance between the rotary disc 104 and wall 108, the space between the wall 108 and rotary disc 104 is tightly sealed.

The driving system for the collecting means will now be described by reference to FIGS. 7 and 8.

A driving power of a motor 110 is transmitted through a pulley 111 mounted on a shaft of the motor 110 and a belt 112 to another pulley 113 to drive a shaft 114 supporting the pulley 113. A gear 115 is mounted to the shaft 114, and this gear 115 is engaged with a gear 124 fixed coaxially with the rotary disc 104 to drive and rotate the gear 124 and the rotary disc 104. A slip mechanism (not shown) including a friction plate is disposed between the gear 115 and the shaft 114, so that when the suction pipe 102 falls in contact with any end of the open groove 107 of the waste store chamber 106, a slip is caused between the gear 115 and the shaft 114. A gear 117 having an arcuate cam groove 116 extending within a certain angle range is mounted on the other end of the shaft 114 rotatably around the shaft 114, and a pin 118 is mounted on the pulley 113 fixed to the shaft 114 so that the pin 118 is freely fitted in the cam groove 116. When the pulley 113 is rotated and the pin 118 moves in the cam groove 116 and hits on any end of the cam groove 116, the gear 117 starts rotation. By the rotation of the gear 117, a gear 119 engaged with the gear 117 is caused to start rotation to actuate or reset the knotter 103.

The knotter 103 has a function of connecting the front end of a fresh sample yarn from the yarn guide 101 to the rear end of the sample yarn to be fed out from the feedout guide 120. Accordingly, the yarn fed out from the knotter 103 through the feed-out guide 120 is a continuous yarn composed of several sample yarns end-to-end connected to one another as shown in FIG. 2. Of course, this knotter 103 includes an element cutting out unnecessary yarn fragments formed by knotting. Any of known yarn knotters such as an automatic knotter for providing fisherman's knots and an automatic knotter for providing weaver's knots can be used in the present invention.

The third element of the collecting means 100 is the yarn feed-out guide 120 for guiding a continuous yarn formed by the knotting operation in the knotter 103 to the subsequent means, namely the storing and feeding means 200. According to a preferred modification, another yarn feed-out guide 121 is disposed separately from the yarn feed-out guide 120, and a tension compensator 122 is located between the two feed-out guides. The tension compensator 122 is a guide capable of swinging under an elastic force. If the yarn tension is low, the tension compensator 122 swings to the left in FIGS. 7 and 8 to enhance the yarn tension, and if the yarn tension is high, the tension compensator 122 swings to the right to adjust the tension by the elastic force. Namely, the tension compensator exerts a function of adjusting the yarn tension within a certain range so as to prevent an abnormal tension from being imposed on the continuous yarn fed to the storing and feeding means perpetually even during the knotting operation.

As an element for ensuring the operation of the collecting means 100 and enhancing the efficiency of said operation, there can be mentioned a reserve guide. This reserve guide has a function of assisting the suction pipe 102 in effectively sucking and holding the intermediate portion of the continuous yarn passing through the yarn guide 101 and the yarn feed-out guide and also a function of securing a length necessary for the nkotting operation in the continuous yarn. If such effects can be imparted to the collecting means 100 by other operation or element, this reserve guide need not be provided. The functions of the reserve guide 123 disposed in the embodiment shown in FIG. 5 will now be described.

A gear 125 fixed to a shaft 126 is engaged with the above-mentioned gear 115 for transmission of the driving power, and a sprocket 127 is attached to the other end of the shaft 126. Further, another sprocket 128 is disposed on the substantially same horizontal plane as that of the sprocket 127, and a chain 129 is laid out between the two sprockets. The reserve guide 123 is fixed to a suitable position on said chain 129. The suitable position means a position at which the following functions can be given to the reserve guide. Namely, the reserve guide is located so that while the suction pipe 102 is rotated to the position where it is connected to the yarn guide 101, the sample yarn 2 from the package is drawn in through the yarn guide 101 and the sample yarn is sucked along a length corresponding to the drawn-in-length into the suction pipe 102, and that when the suction pipe 102 is rotated in the reverse direction indicated by an arrow B in FIG. 6, the drawn-in sample yarn is gradually discharged. By virtue of these functions of the reserve guide, it is made possible to secure yarn lengths necessary for the knotting operation and prevent occurrence of such undesirable phenomena as yarn entanglement and generation of excessive tension.

Figure 9:
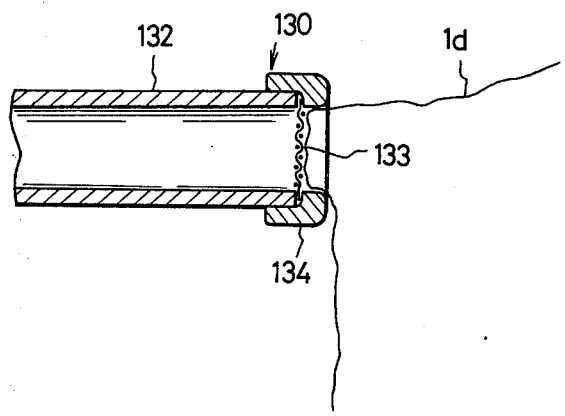
FIG. 9 is a view showing the longitudinal section of a sample yarn reserve opening.

In FIG. 5, reference numeral 130 represents a sample yarn reserver having a suction opening on which a sample yarn to be substantially fed is temporarily sucked and held. A switch 131 is disposed to actuate this sample yarn reverve opening 130. The longitudinal section of the reserver 130 is illustrated in FIG. 9. A net 133 is pressed to the top end of a cylinder 132 by means of a cap 134. This cylinder 132 is communicated with said waste store chamber 106. Accordingly, air is sucked from this reserve opening. Therefore, for example, when a sample yarn of a package 1c is collected through the yarn guide 101 and the suction pipe 102 is separated from the yarn guide 101, a sample yarn of a package 1d, which is to be collected next, is sucked to the reserver 130, whereby the sample yarn from the package 1c is held on the reserver 130 and is suspended on and along the front face of the front end 101A of the yarn guide 101.

The storing and feeding means and the present counter actuated in response to the operation of the storing and feeding means will now be described.

A typical instance of the storing and feeding means 200 is illustrated in FIG. 10, partially in section. The storing and feeding means includes a storing drum 201 capable of winding a continuous yarn thereon. The continuous yarn is fed to the storing drum 201 from the peripheral direction and a certain quantity of the continuous yarn is wound on the storing drum 201. Thus, a certain quantity of the continuous yarn can be stored on this drum 201. Further, the storing drum 201 is arranged so that the stored continuous yarn can be continuously taken out from the axial direction thereof. Moreover, storing drum 201 is designed so that the speed for winding thereon the continuous yarn is higher than the speed for taking out the continuous yarn therefrom.

The preset counter 300 has a function of counting the quantity or length of the continuous yarn stored in the storing and feeding means 200.

Storing and Feeding Means

As shown in FIG. 10, the storing drum 201 is a rotary drum having a plurality of slits 203 formed in a comb-like shape to extend from one end of the drum to the vicinity of the lengthwise center of a rotation shaft 202 of the drum 201. When a pulley 204 attached to one end of the rotation shaft 202 is rotated, the storing drum 201 is rotated. The rotation shaft 202 is supported by a bearing 206 attached to a frame 205 of the storing and feeding means 200. The pulley 204 is arranged so that when a motor 207 attached to the frame 205 is turned, the pulley 204 is rotated through a pulley 208 and a belt 209. The motor 207 has an instant stop mechanism and when the motor 207 receives specific instructions described hereinafter, it stops instantly and rotates again. On the side of the bearing 206, the storing drum 201 has an inclined ring 211 having a projection 210 or the like projected from the outer circumference of the drum 201. This inclined ring 211 is disposed so that it can incline to the rotation shaft 202 and can be rotated with rotation of the storing drum 201. Namely, a fixed shaft 212 capable of inclining is set at the rotation center of the inclined ring 211, and it is attached to the frame 205 through a bracket 213. A bearing 214 is attached around the fixed shaft 212, and it is inclined with a pin 215 attached to the rotation shaft 202 being as the center. A spring 216 which is elongated according to the winding pressure on the continuous yarn is laid out between the fixed shaft 212 and another bracket 217 attached to the frame 205. A detector 218 is mounted on the top end of the bracket 217 to indicate that during the sample yarn storing operation described hereinafter, the inclined ring 211 is rectangular to the rotation shaft 202, namely the state where a continuous yarn in a length exceeding a certain critical length is stored on the storing drum and the spring cannot resist the winding pressure thereof any more, and the inclination degree of the inclined ring 211 is reduced. For example, a limit switch is used as the detector 218. The above state detected by the detector 218 is determined by the quantity of the wound continuous yarn and the strength of the spring.

Radially extending projections 219 on the inclined ring 211 project slightly over the surface of the storing drum 201 through slits 203 of the storing drum 201. For simplification of illustration, one projection is now selected from many projections of the inclined ring and its movement is described. With rotation of the storing drum, the projection 210 slides in the slit 203 along the rotation shaft 202. In the state shown in FIG. 10, the projection on the right side is closest to the front portion 201A of the storing drum 201 and the projection 210 on the left side is most separated therefrom. In the process of winding the continuous yarn on the storing drum, if the point at which the continuous yarn begins to fall in contact with the storing drum 201 is in the region where the projection 210 of the inclined ring 211 is sliding, for example, in the region where the projection 210 is separated from the front portion 201A of the storing drum 201 as shown in FIG. 10, then the continuous yarn which has fallen in contact with storing drum 201 and has been wound thereon is pushed out to the point closest to the front portion 201A while the inclined ring 210 makes ½ rotation together with the storing drum 201. The above procedures are similarly repeated continuously and the wound continuous yarn is pushed out in succession within a certain range of the wind number.

On the side of the front portion 201A, a featherlike unwinding tension stabilizing ring 219 is attached to the periphery of the storing drum 201, and a guide 220 is mounted at a position slightly separated from said front portion 201A and very close to the rotation center of the rotation shaft 202, so that the continuous yarn wound on the storing drum 201 and pushed out to the side of the front portion 201A is unwound and taken out through said guide 220. This state will readily be understood from FIG. 11.

A photoelectric detector tube 222 for detecting the frequency of generation of ballooning which takes place between the front portion 201A and guide 220 when the continuous yarn is unwound from the storing drum 201 is mounted on a frame 221 to which the guide 220 is attached. Preferably, two sets of such photoelectric detector tubes 222 are disposed. FIGS. 11, 12 and 13 illustrate embodiments where one set or two sets of photoelectric detector tubes are disposed to detect generation of ballooning 223.

Every time ballooning takes place, its locus interferes with the transmission region between a projector 222A of the photoelectric detector tube 222 and a receiver 222B of the photoelectric detector tube 222. The position of the optical axis is limited to the vicinity of the surface of the guide plane and ballooning is restricted in a linear form in this region. Accordingly, one signal is emitted every time ballooning takes place. The winding number of the continuous yarn on the storing drum 201 can be known from the frequency of this interference. Namely, the frequency of the interference can be a function of the length or quantity of the continuous yarn being fed to the subsequent testing means. When two sets of photoelectric detector tubes are disposed as shown in FIG. 13, the direction of ballooning can also be detected. For example, if the frequency of ballooning taking place in the winding direction is $n$ and the frequency of ballooning taking place in a direction reverse to the winding direction is $n'$, the increase $m$ of the winding number on the storing drum 201 can be calculated according to the formula of $m = n - n'$. This ballooning detecting method is very advantageous for always inspecting the quantity of the stored yarn accurately. As a simple method for always inspecting the wound quantity, there can be mentioned a method in which the length of the yarn taken out and the length of the wound yarn are simply measured and the wound quantity is determined from the difference between the measured lengths. Because of elastic characteristics of the yarn, however, it cannot be said that the thus determined wound quantity will correspond strictly to the actual wind number of the yarn on the storing drum. Accordingly, in this method, there is a risk that errors will be accumulated, and according to this method, it is difficult to always inspect the wound quantity of the yarn correctly. This defect can be effectively eliminated by the abovementioned balloon detecting method.

Preset Counter

The preset counter 300 is mounted on the storing and feeding means 200. Any of elements capable of detecting the length or quantity of the continuous yarn fed to the storing and feeding means 200 from the collecting means 200 can be used as the counting element of the preset counter 300. However, it is preferred that the counting element of the preset counter 300 be an element capable of counting the absolute rotation number of a rotary member rotating while falling in contact with the running continuous yarn. As shown in FIG. 11, the rotation number of the pulley 204 attached to the top end of the rotation shaft 202 of the storing drum 201 is detected by the preset counter 300 comprising a small magnet piece 225 attached to the pulley 204, a reed switch 301 and a counter 302. The length of the continuous yarn fed to the storing drum 201 is calculated from the detected rotation number and the length of the outer circumference of the storing drum 201.

Operations

The basic structure and mechanism of the apparatus of the present invention and preferred modification thereof have been illustrated. Now, the operations of the apparatus of the present invention will be described in detail.

In the apparatus of the present invention, the operation X of collecting many sample yarns having a certain length and connecting them in succession to one another in an end-to-end manner to form a continuous yarn is performed by the collecting means 100, and the operation Y of winding the so formed continuous yarn coordinately with the operation of the collecting means 100 and the operation Z of feeding the continuous yarn continuously to the testing means 5 are performed by the storing and feeding means 200. Each of the operation X of forming a continuous yarn and the operation Y of winding and storing the so formed continuous yarn should naturally include an operation of stopping running of the continuous yarn, as will be apparent from the foregoing illustration. On the other hand, the operation Z of feeding the continuous yarn is conducted without stopping running of the continuous yarn. Moreover, such different operations Y and Z are performed in one device, namely the storing and feeding means 200.

These operations are conceptually illustrated in FIGS. 14-A to 14-C. FIG. 14-A illustrates the state where a sample yarn 2 is collected in the collecting means 100 and simultaneously, in the storing and feeding means 200, a continuous yarn having a knot 3 is unwound from the storing drum and fed to the testing means at a speed of $V_1$. In this state, running of the continuous yarn 4 from the collecting means 100 is stopped. FIG. 14-B illustrates the state where the sample yarn 2 and continuous yarn 4 are end-to-end connected to form a continuous yarn by the operation X in the collecting means and simultaneously, in the storing and feeding means, the continuous yarn is fed at a speed of $V_1$ to the testing means. Since the continuous yarn is not fed to the storing and feeding means 200 from the collecting means 100 in this state, the quantity of the continuous yarn stored in the storing drum is reduced and is smaller than in the state shown in FIG. 14-A. FIG. 14-C illustrates the state where the operation X such as knotting has been completed in the collecting means 100 and in the storing and feeding means 200 the continuous yarn is transferred at a transfer speed of $V_2$ (namely, the speed for winding the continuous yarn on the storing drum) while the continuous yarn is fed to the testing means at a speed of $V_1$. In the apparatus of the present invention, since the relation of $V_2 > V_1$ is established, even if the continuous yarn is unwound from the storing drum and is fed to the testing means, the continuous yarn is stored on the storing drum again and the amount of the continuous yarn stored in the storing and feeding means 200 is increased and is larger than in the state shown in FIG. 14-C.

Specific operations of collecting sample yarns having a constant length from packages 1 and connecting them to one another in an end-to-end manner by using the above-mentioned collecting means 100 will now be described.

A sample yarn of one of packages 1, for example, a package 1c, is inserted into the front end 101A of the yarn guide 101 through the pig tail guide 14c of the guide stand 13 as shown in FIG. 5. In the case where the yarn guide 101 has a long tubular form, it is difficult and troublesome to pass the yarn through this guide 101. Accordingly, in the state where the suction pipe 102 is connected to the yarn guide 101, namely in the state indicated by two-dot chain lines in FIG. 7 and 8, the end of the sample yarn is sucked to the yarn guide 101, and then, the suction pipe 102 is manually turned to the left, namely in the direction of arrow B in FIG. 6. Then, the yarn end is taken out from the yarn guide 101 to complete passage of the sample yarn through the yarn guide. During this operation, the collecting means is controlled so that it is prevented from automatically starting its operation. The yarn 4 from the yarn guide 101 is passed through the yarn feed-out guide 120, tension compensator 122 and guide 121 and is led to the storing and feeding means 200 and then to the testing means 5. Thus, the sample yarn has been passed through all the means of the apparatus of the present invention, and preparation for starting of the apparatus has been completed.

Then, control signals are given to the apparatus so that it is automatically operated. At first, start signals are given to the storing drum 201 and testing means. The start signal for the storing drum 201 is transmitted from the collecting means 100 on completion of the knotting operation. When the storing drum 201 is rotated on receipt of the start signal, the magnet piece 225 is simultaneously rotated and rotation of the magnet piece 225 is detected and counted as the rotation of the storing drum by the reed switch 301. When the thus counted rotation number of the storing drum 201 is elevated to a level corresponding to a predetermined yarn length of the counter 302, rotation of the storing drum 201 is stopped and simultaneously, counting of the rotation number is stopped. Thus, collection of the sample yarn of the package 1c has been completed. Although the rotation of the storing drum 201 has thus been stopped, the yarn is still unwound therefrom and is continuously fed to the testing means 5, as illustrated hereinbefore.

Then, collection of a sample yarn of the package 1d is conducted as shown in FIG. 5. First, the sample yarn of the package 1c is cut in the vicinity of the front end 101A of the yarn guide 101. The subsequent sample yarn 1d has already been sucked and held on the reserve opening 130, and the end of the sample yarn 1d is suspended in front of the front end 101A of the yarn guide 101. In this state, a starting signal is given to the motor 110 to rotate the motor 110. Simultaneously, the rotary disc 104 starts rotation. Namely, the rotary disc 104 and suction pipe 102 are turned from the positions indicated by solid lines in FIGS. 6 and 8 to the positions indicated by chain lines. Simultaneously, also the sprockets 127 and 128 are rotated, and the chain 129 and the reserve guide 123 fixed thereto are shifted from the positions indicated by solid lines in FIG. 7 to the positions indicated by chain lines. (The shifted reserve guide is represented by reference numeral 123'.) Accordingly, the continuous yarn which has been present between the yarn feed-out guide 120 and the tension compensator 122 is caused to run along a yarn passage indicated by two-dot chain lines in FIG. 7 by the reserve guide 123. Accordingly, a small quantity of the sample yarn of the package 1c left in the yarn guide 101 is drawn in.

When the suction pipe 102 attached to the rotary disc 104 falls in contact with the yarn guide 101, rotation of the rotary disc 104 is stopped, and therefore, air which has been sucked from the suction pipe 102 begins to be sucked from the front end 101A of the yarn guide 101. Accordingly, the end portion of the sample yarn of the package 1d suspended before the front end 101A and the cut end portion of the sample yarn of the package 1c are sucked into the waste store chamber 108 through the yarn guide 101 and suction pipe 102.

Figure 8:
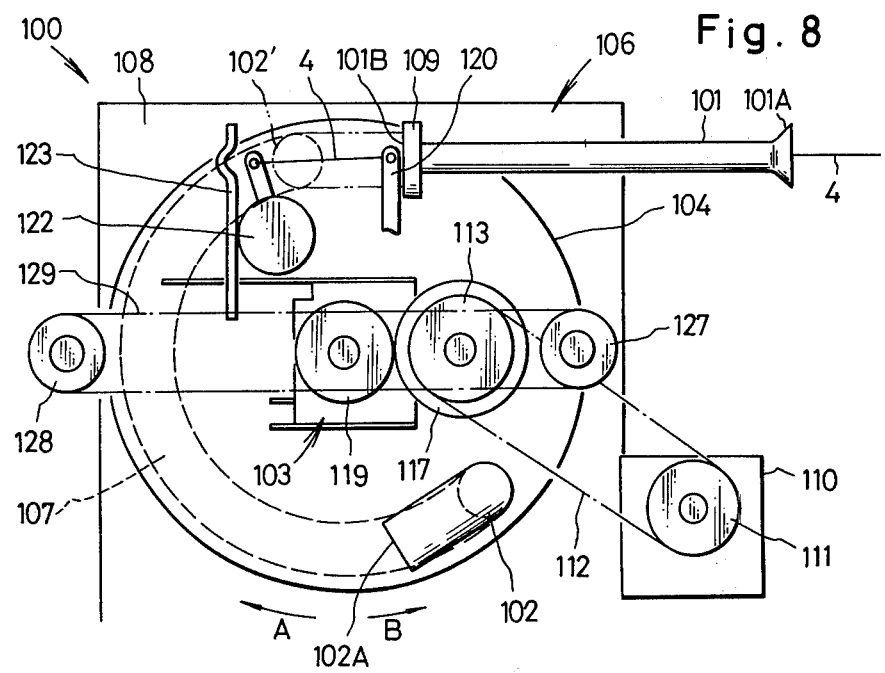
FIG. 8 is a side view illustrating the sample yarn collecting means.

Then, the rotary disc 104 is returned to the position indicated in FIGS. 6 and 8. At this point, the suction pipe 102 having the ends of the two sample yarns sucked therein are turned around the knotter 103 though only partially. Accordingly, when the suction pipe 102 is turned to the position indicated by solid lines in FIG. 6, the ends of the two sample yarns are inserted into the knotter 103. Namely, as shown in FIG. 6, the two sample yarns are correctly set at the knotting position of the knotter 103. The motor 110 is further rotated, but when the knotter 103 is actuated after the above yarn guiding operation and the knotting operation are completed, the rotation of the motor 110 is stopped. Thus, the sample yarn collecting and knotting operations have been completed, and a knot $k$ indicated by two-dot chain lines in FIG. 6 is formed and a signal for starting the take-out operation is transmitted to the storing and feeding means 200.

Now, operations of the storing and feeding means 200 will be described specifically. When a start signal is transmitted to the knotter 103, the preset counter 300 is simultaneously reset. When the knotting operation started by the above signal is completed, a rotation-starting signal is transmitted to the storing drum 201, and the storing drum 201 starts rotation. With this rotation of the rotary drum 201, the stored continuous yarn is unwound from the front end 201A of the rotary drum 201 and fed to the testing means 5 while the continuous yarn from the collecting means 100 is being wound on the storing drum 201.

When a trouble is caused in the collecting means 100, rotation of the storing drum 201 is stopped and counting by the preset counter 300 is simultaneously stopped. After the trouble has been expelled, the storing drum 201 starts rotation again.

Stop signals are transmitted to the storing drum 201 in the following manner.

(A) When the wound yarn length arrives at a predetermined value of the preset counter 300, a stop signal is transmitted from the preset counter.

(B) When the storing drum 201 becomes full of the continuous yarn, a detecting member on the rotary drum 201 transmits a stop signal to the storing drum 201. For example, a stop signal is transmitted from a detecting member detecting the contact between the inclined ring 211 and limit switch 218 or a computing member for computing the stored quantity from the frequency of occurrence of ballooning detected by the photoelectric detector tube 222 or from the rotation number of the storing drum 201 or motor 110.

(C) When a trouble such as yarn breakage or abnormal tension is caused in the collecting means 100, a stop signal is transmitted to the storing drum 201 from the collecting means 100.

In the apparatus of the present invention, after the preset counter 300 transmits instructions of stopping rotary drum 201 when the stored yarn length arrives at the predetermined value or after it transmits instructions of starting the knotting operation to the collecting means 100, the preset counter 300 is reset, and when the storing drum 201 receives a start signal on completion of the knotting operation, the preset counter 300 starts counting. When the rotary drum 201 is full of the continuous yarn or a trouble is caused in the yarn collecting means 100 while the preset counter 300 continues counting, the counting is interrupted and the counted value is maintained as it is until the rotary drum 201 starts rotation again. In this case, when counting is started again after stoppage owing to full drum, in order to prevent hunting, it is preferred to start counting after a certain lag.

Figure 15:
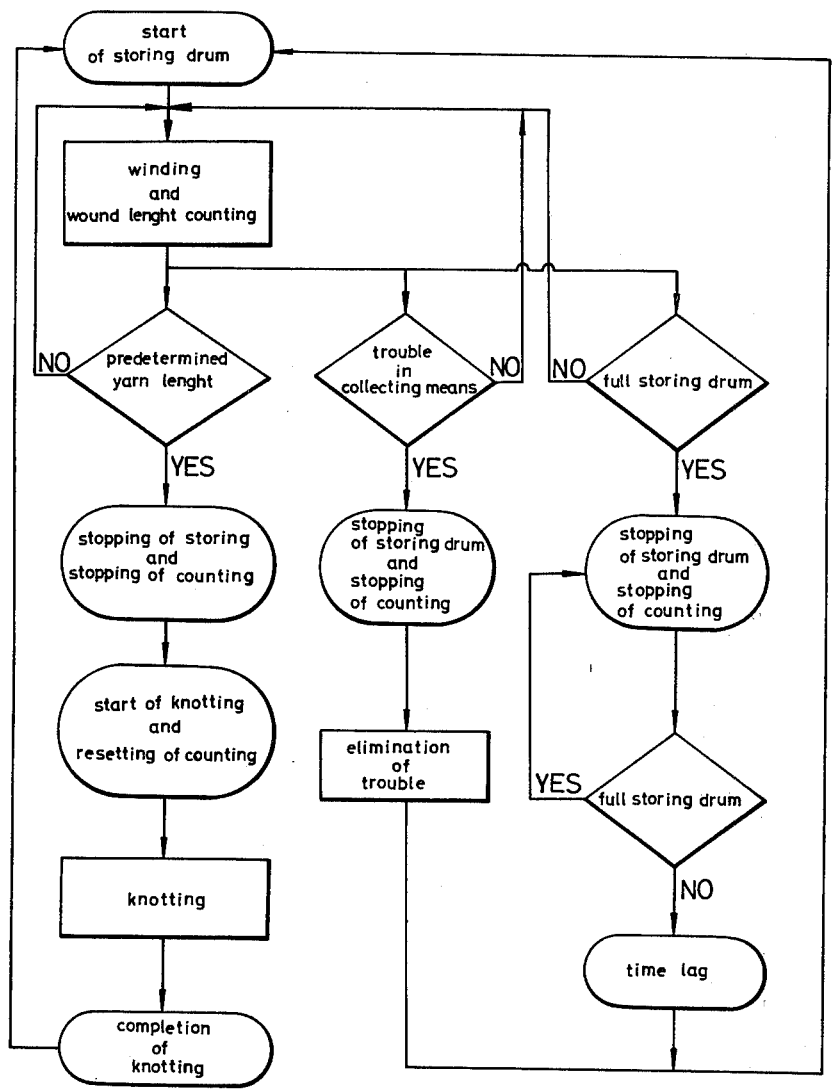
FIG. 15 is a flow chart of operations in the apparatus of the present invention.

In the apparatus of the present invention, by the foregoing related operations of the collecting means 100, storing and feeding means 200 and preset counter 300, a continuous yarn is continuously fed to the testing means 5 from the storing drum 201 while increasing and decreasing the quantity of the continuous yarn stored on the storing drum 201 repeatedly, and sample yarns having a certain length are collected and connected to one another while rotation of the storing drum 201 is stopped. These operations are illustrated in the flow chart of FIG. 15.

Other Embodiments

In the present invention, modifications such as mentioned below may be made to the above-mentioned respective means and elements thereof.

Package Hanging Means

Figure 16:
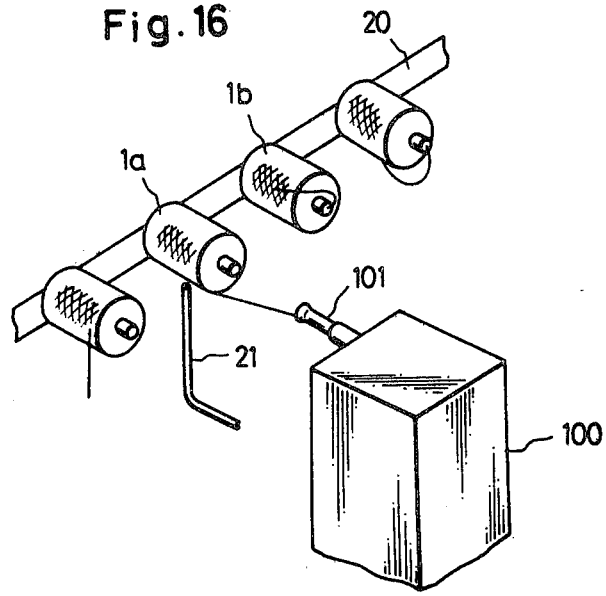
FIGS. 16 to 18 are diagrams illustrating other embodiments of the package hanging means.

Sample yarns may be collected from packages 1 delivered in a direction indicated by an arrow by a conveyor 20 as shown in FIG. 16. In each of packages 1, the yarn end has been taken out in advance and it is set so that it traverses the package. When a package 1a from which a sample yarn is to be collected is stopped in front of collecting means 100, a telescopic yarn guide 101 is expanded to suck the yarn end, and after sucking of the yarn end, it is contracted. Since the guide 101 is contracted to a position suitable for unwinding the yarn from the package 1a, the sample yarn is conveniently collected and then knotted. When the collecting operation is thus completed, the conveyor 20 is moved again so that the subsequent package 1b is located in front of the collecting means 100. At this point, the end portion of the sample yarn collected from the package 1a is cut by a hot line cutter 21.

Figure 17:
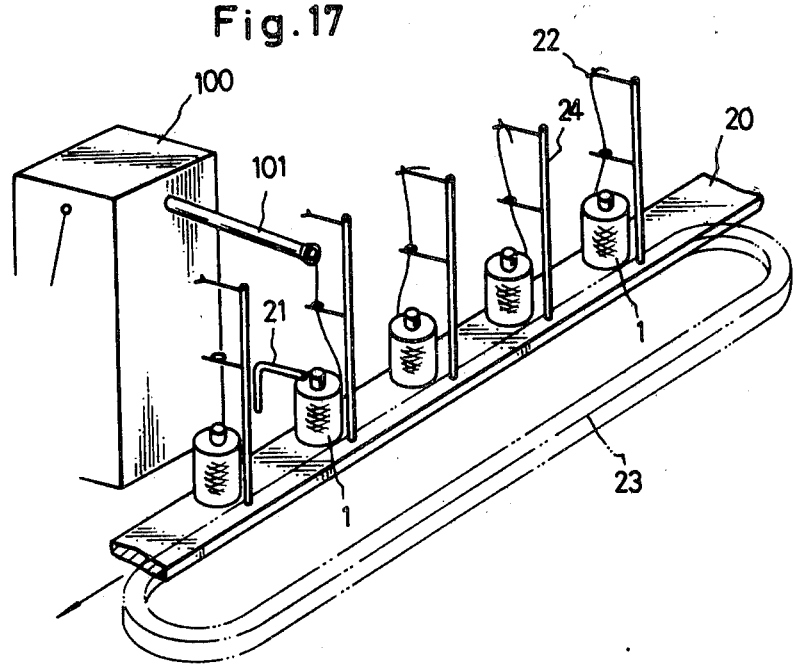

Another embodiment in which a sample yarn is collected from a package 1 delivered in a direction indicated by an arrow in FIG. 17 by a conveyor 20 is illustrated in FIG. 17. The conveyor 20 has a rising guide 24 and a yarn holder 22 for each package 1, and the yarn end of the package 1 has been taken out in advance and is set on the holder 22 through the guide 24. In this embodiment, the guides 24 and yarn holders 22 are fixed to the conveyor 20, but the embodiment may be modified so that another small conveyor 23 disposed independently is moved synchronously with the conveyor 20 as indicated by two-dot chain lines. In this modification, these guides make no hindrance to operations at preceding and subsequent steps.

Figure 18:
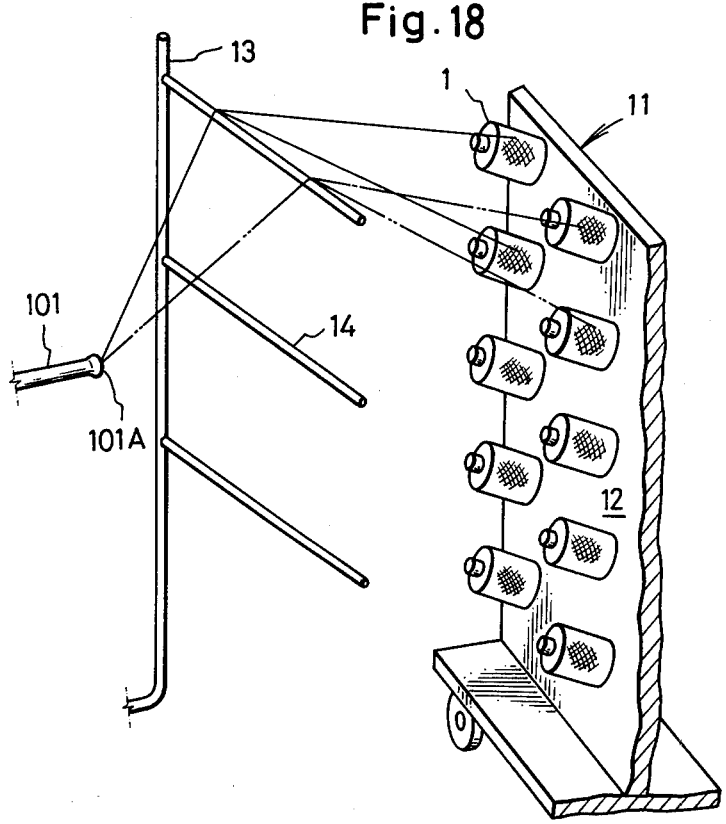

A guide stand as shown in FIG. 18 may be used as well as the guide stand as shown in FIG. 5.

Collecting Means

Figure 19:
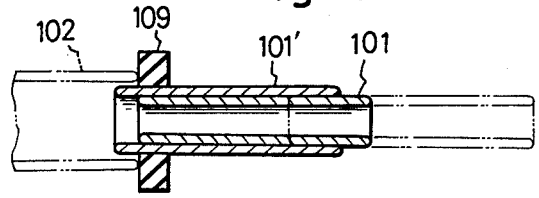
FIGS. 19 to 22 are diagrams illustrating other embodiments of the yarn introduction guide.
Figure 20:
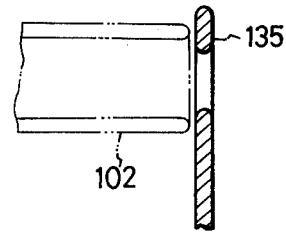
Figure 21:
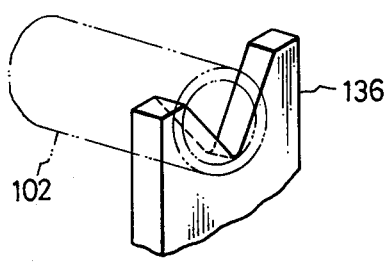

In general, the yarn guide 101 is a straight pipe. So far as the connection to the suction pipe 102 is not inhibited, a modification as shown in FIG. 19 may be adopted according to need. In FIG. 19, an outer pipe 101' is set on the outside of the pipe 101 to form a telescopic guide member. Moreover, bent pipe or flexible pipe having a sufficient low resistance to running of the yarn may be used as the yarn guide 101. Still further, a perforated plate 135 as shown in FIG. 20 or a V-shaped guide 136 as shown in FIG. 21 may be disposed as the yarn guide.

Figure 22:
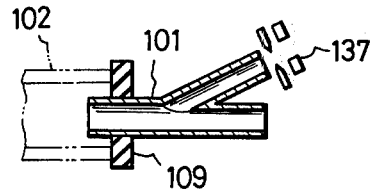

In the case where the collecting means 100 collects a sample yarn from a specific package frequently as the standard yarn, there may be adopted an embodiment as shown in FIG. 22, where a branched pipe 101 is used as the yarn guide and a yarn holding and cutting device 137 is disposed as an additional element at the part for introduction of the yarn from the specific package.

Figure 23:
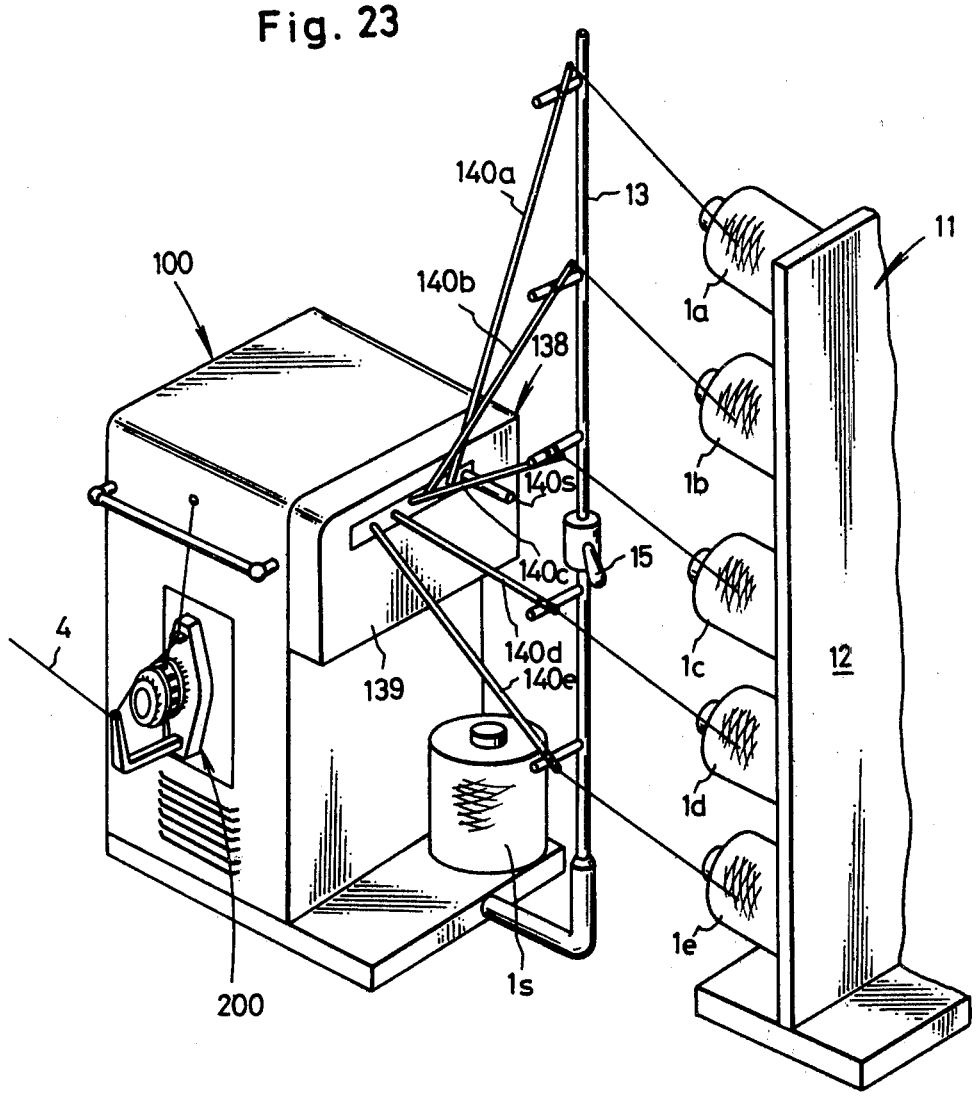
FIG. 23 is a perspective view illustrating another embodiment of the apparatus of the present invention in which a yarn changeover machine is included.

Still further, means for performing effectively the so called yarn cutting operation of feeding yarns of packages one by one in succession to the yarn guide, for example, a package changeover machine, may be combined as an additional mechanism with the apparatus of the present invention. This embodiment is illustrated in a perspective view of FIG. 23. This package changeover machine will now be described by reference to FIG. 23.

The package changeover machine 138 comprises a yarn sucking unit 139 and a plurality of yarn sucking tubes 140 (140a, 140b, . . . 140s). The ends of sample yarns of packages 1a, 1b, . . . and a standard yarn sample of a standard yarn package 1s are sucked to these sucking tubes, and one of these sample yarns is passed through the yarn guide 101. When collection of one sample yarn is completed, the sample yarn is cut between the yarn guide 101 and the yarn sucking tube 140 by a cutter disposed in the suction unit 139, and another sample yarn sucked in the corresponding yarn sucking tube is then introduced in the yarn guide 101 and passed therethrough by a suitable mechanism installed in the suction unit 139. Each yarn sucking tube 140 is extended to the guide position on a guide stand 13. The number of the tubes 140 is the same as the stage number of the package hanging means 11. Another short sucking tube 140s is disposed as the guide for collecting the standard yarn sample. The structure of the suction unit 139 will now be described by reference to FIG. 24 (top plan view) and FIGS. 25-A and 25-B (sectional views taken along the line XXVA—XXVA and the line XXVB—XXVB of FIG. 24, respectively).

Reference numerals 151, 152 and 153 represent fixed plates, and a sliding block 155 provided with a shear cutter 154 is allowed to slide among them. Six short tubes 156 are mounted on the fixed plate 151, and they are connected to the sucking tubes 140 through joint tubes 157. A tube 158 is communicated with the waste chamber and a sucking force is always applied to the tube 158. A cutter 154 is pressed by a spring 159. When the sliding block 155 slides, the cutter 154 cuts the yarn through the tube 158 with a cutting corner *a* and the yarn through the plate 153 with a corner *b* as shown in FIG. 25-B. After the yarn guide 101 is connected to the fixed plate 153, the above movement of the sliding block 155 is accomplished by a motor 160 through a gear 161. A limit switch 162 is mounted to determine the stop position of the block 155. When this multi-way yarn sucking unit is employed, all the yarns except one being collected are sucked and held by the tube 158. When the sample yarn in which sampling has been completed is cut between the package and guide stand 13, the yarn end on the side of the sucking tube 140 is sucked into the waste chamber. Accordingly, the yarn end of the adjacent package on the same stage, from which a sample yarn is now to be collected, is sucked to the tube 140. Thus, one cycle of the package changeover operation is completed. Yarns in which sampling has been completed are similarly cut in succession, and cut ends are sucked to the tubes. This changeover operation can be performed conveniently if an arrangement is made so that a lamp on the sucking tube 140 corresponding to the yarn being sampled is lighted during the sampling operation. When it is desired to temporarily stop the action of the sliding block 155 for shifting of the hanging means or other purposes, the temporary stop switch 5 is put on.

When the above-mentioned multi-way yarn sucking unit is added to the apparatus of the present invention, the following advantages can be attained.

(1) Since suction openings are disposed for respective stages, the sequence of sample yarns is not confused at all.

(2) It is not required at all that collection of one sample yarn should be completed within a predetermined time. Even in the case where the operation is retarded to some extent in the midway, if the dealy is recovered by accelerating collection of subsequent sample yarns, reduction of the processing efficiency can be prevented. Accordingly, even an operator having a less experience can operate the system with ease and can perform the operation at a high efficiency.

Storing and Feeding Means

Figure 26:
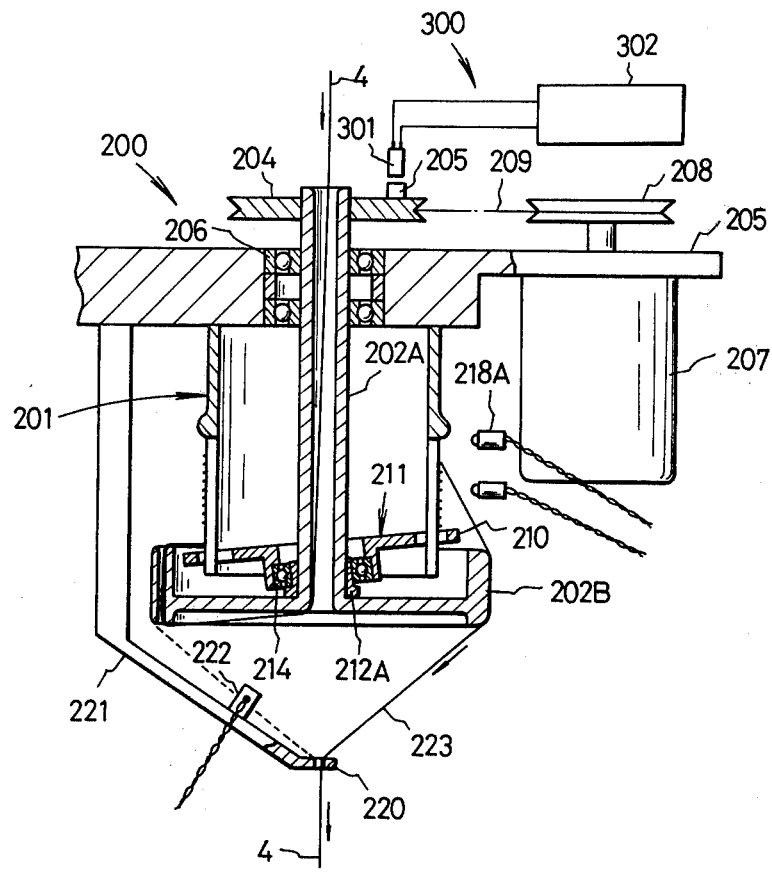
FIG. 26 is a sectional view showing another embodiment of the storing and feeding means which is to be included in the apparatus of the present invention.

In the embodiment shown in FIGS. 10 and 11, the storing drum 201 is rotated in the storing and feeding means. In the present invention, there may be adopted storing and feeding means of the type in which the storing drum 201 is fixed. This modification is illustrated in FIG. 26. The storing drum 201 is fixed to the frame 205, and a rotary shaft 202A is disposed through the storing drum 201 and the shaft 202A is rotated. On the side opposite to the side where the frame 205 is present, slits are formed on the storing drum 201 along the center line of the rotary shaft 202A. The rotary drum 202 has a hollow structure, and a yarn path is formed in the hollow portion. A wedge-like guide desk 202B is mounted on the top end of the rotary shaft 202A. A boss 212A inwardly eccentric from the guide desk 202B toward the frame 205 is fixed to the top end portion of the rotary shaft 202A, and the inclined ring 211 is attached to the boss 212A through the bearing 214. Projections or like members 210 sliding in the slits of the storing drum 201 are disposed on the periphery of the inclined ring 211. A detector 218A is mounted on the outer circumference of the storing drum 201 to detect the quantity of the continuous yarn stored on the rotary drum 201. A guide 220 is disposed in the front of the storing drum 201 on the axial line of the rotary shaft 202A.

In this embodiment, the continuous yarn 4 passes through the hollow portion of the rotary shaft 202A and through the guide hole of the guide desk 202A and is wound on the periphery of the fixed storing drum 201. With rotation of the rotary shaft, the eccentric boss 212A is rotated, and therefore, with rotation of the eccentric boss 212A, the inclination angle of the inclined ring 211 is changed without rotation thereof. As a result, the continuous yarn 4 wound on the storing drum 201 is pushed toward the frame 205 and stored.

The stored continuous yarn is then fed to the testing means 5 through a guide 220 while forming a balloon on the outermost periphery of the guide desk 202B.

As in the embodiment shown in FIG. 10, a photoelectric detector tube 222 is mounted on a frame 221 to count the frequency of occurrence of ballooning caused between the guide desk 202B and guide 220 when the continuous yarn is unwound from the storing drum 201. Supposed that the frequency of occurrence of ballooning is n and the rotation number of the pulley 204 counted by the reed switch 301, namely the rotation number of the guide desk 202B, is a, the quantity m of the yarn stored on the storing drum 201 is expressed by the formula of $m = a - n$.

In the storing and feeding means 200 of the apparatus of the present invention, the length of a sample yarn collected from one package is set as the rotation number of the storing drum 201 in the preset counter 300. If a higher accuracy is required and a unit length to be measured is smaller than the circumferential length of the storing drum 201, a plurality of small magnet pieces 225 are disposed on the periphery of the pulley 204, whereby the intended high accuracy can be conveniently attained.

Figure 27:
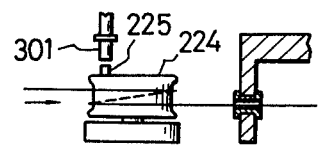
FIG. 27 is a diagram illustrating another embodiment of the means for measuring the length of the yarn to be stored.

Further, there may be adopted a modification where a driven rotary roller 224 which is rotated by running of the yarn is disposed on the inlet side of the storing drum 201 and the yarn is travelled in the state wound on this roller 224 as shown in FIG. 27. In this embodiment, the length of the yarn wound on the storing drum 201 can be counted as the rotation number of the roller 224 by a small magnet piece 225, a reed switch 301 facing to the magnet piece 225 and a counter 302.

In the embodiments illustrated hereinbefore, the storing and feeding means is disposed after the collecting means, and this storing and feeding means continuously feeds the continuous yarn to the subsequent testing means while receiving the continuous yarn thereon from the collecting means.

Figure 7:
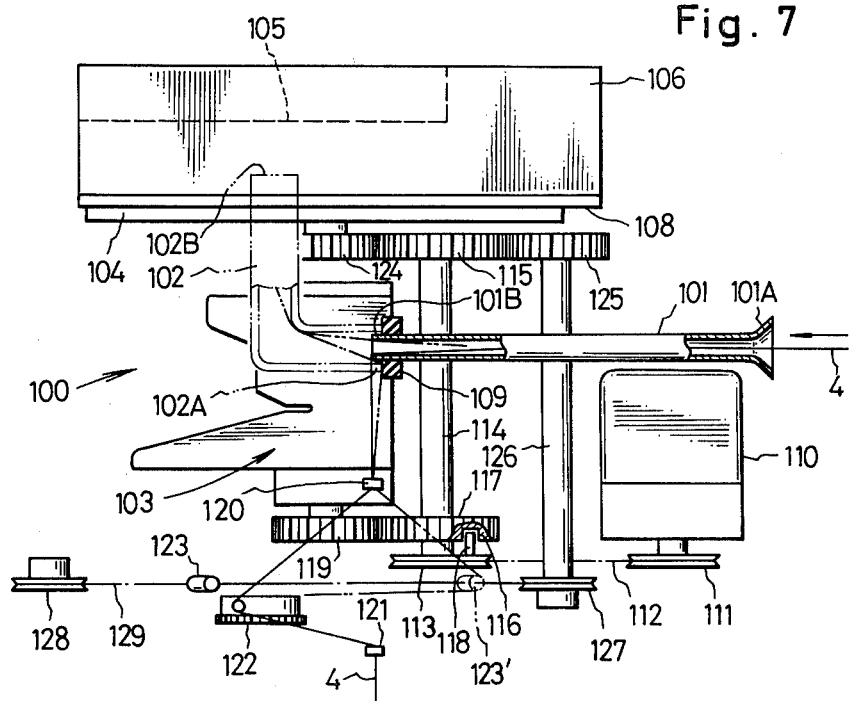
FIG. 7 is plan view illustrating the sample yarn collecting means.
Figure 28:
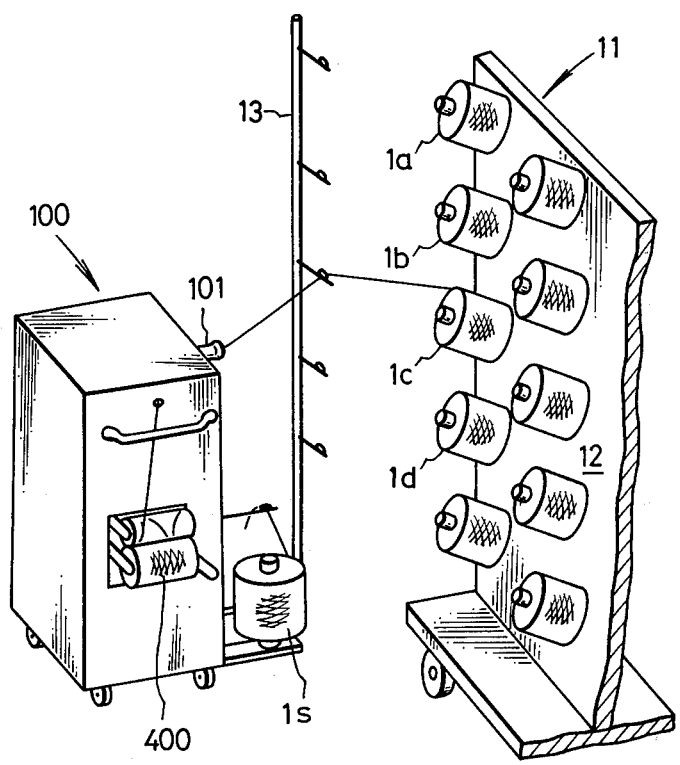
FIG. 28 is a diagram illustrating still another embodiment of the apparatus of the present invention in which a winder is included instead of the storing and feeding means.

In the present invention, a customary winder may be disposed instead of the storing and feeding means connected to the collecting means shown in FIGS. 6, 7 and 8. FIG. 28 illustrates this embodiment in which a winder 400 is disposed instead of the storing and feeding means.

In this case, a continuous yarn is once wound in the form of a cheese, and it is then fed to the predetermined testing means. If a transfer tail is formed on each cheese and these transfer tails are knotted, sample yarns can be continuously fed to the testing means. Further, since sample yarns are once wound in the form of a cheese, one collecting means need not necessarily be disposed for every testing means, and therefore, a large flexibility can be secured with respect to the operation of the apparatus. Moreover, the versatility of the entire system is increased, and for example, the testing means can be disposed at a place distant from the collecting means.

As will apparent from the foregoing illustration, by using a mechanical knotter, changeover knotting can be accomplished very promptly while attaining the foregoing advantages, only by very simple operations of causing a yarn guide communicated with sucking and holding means to suck thereon the end of a sample yarn of a package to be tested, cutting the sample yarn at a desirable position after the sampling operation and sucking the end of a subsequent sample yarn to the cut end of the thus collected sample yarn. Accordingly, the present invention provides a sample yarn collecting apparatus of a very simple structure having very excellent characteristics not possessed by the conventional apparatus.

In the apparatus of the present invention, processing of yarn ends is very simple. Therefore, the apparatus of the present invention can be directly connected to an automatic package delivery line.

Further, when the storing and feeding means of the present invention is used, since the step of collecting sample yarns from packages can be directly connected to the testing means, in which stopping of the yarn is not allowed, through this storing and feeding means, all the operations can be simplified and sample yarns can be fed in order without confusion of the sequence. Still further, even if there is a great difference of the treatment capacity between the collecting means and the testing means, since the collecting operation can be performed concentratedly and intermittently, the operation efficiency can be enhanced, and even if a trouble is caused in the knotting operation or the like, the trouble can be eliminated without being pressed for time while continuing feeding of the yarn to the testing means smoothly. Still in addition, since the tension on the yarn being fed to the testing means can be stabilized, merits can be attained also with respect to the test accuracy.

What is claimed is:

1. An apparatus for preparing a continuous test yarn composed of end-to-end connected sample yarns having a certain length, comprising (1) sample yarn collecting means which collects sample yarns having a certain length from a plurality of yarn packages and connects each of them to one another in an end-to-end manner to form a continuous yarn, (2) means for storing and feeding said continuous yarn, said storing and feeding means including a storing drum on which the continuous yarn is stored by introducing the continuous yarn from the peripheral direction of said drum and winding a predetermined quantity of the continuous yarn on the drum and from which the stored continuous yarn is continuously taken out from the axial direction of the drum, the speed for winding the continuous yarn on the storing drum being higher than the speed for taking out the continuous yarn from said storing drum, and (3) a preset counter for indicating and counting a predetermined length of the continuous yarn stored in said storing and feeding means by one storing operation, wherein said preset counter transmits a signal when said storing and feeding means completes storing of the predetermined length of the continuous yarn, to instruct said storing and feeding means to stop the yarn storing operation and to instruct said sample yarn collecting means to prepare for the yarn connecting operation, and wherein said sample yarn collecting means transmits a signal on completion of the sample yarn collecting and connecting operation to cause said storing and feeding means to initiate the yarn storing operation.

2. An apparatus as set forth in claim 1 wherein means for reading the rotation number of the storing drum is disposed and a signal of the rotation number generated by said reading means is transmitted to said preset counter as the count signal.

3. An apparatus as set forth in claim 2 wherein at least one small magnet piece is attached to the side portion of the storing drum and a reed switch is disposed to face said small magnet piece, whereby the rotation number of the storing drum is counted.

4. An apparatus as set forth in claim 1 including means for counting the number of balloonings of the continuous yarn taken out from the storing drum to thereby inspect the quantity of the continuous yarn stored on the storing drum.

5. An apparatus as set forth in claim 1 wherein a plurality of the yarn packages are hung on a hanging stand.

6. An apparatus as set forth in claim 1 wherein a plurality of the yarn packages are arranged on an intermittently moving conveyor.

7. An apparatus for preparing a continuous test yarn composed of end-to-end connected sample yarns having a certain length, comprising (1) sample yarn collecting means including (i) a yarn introduction guide, the front end of which guides and introduces sample yarns, (ii) a suction pipe which is movable so that the inlet of said pipe on the suction side is operated to be connected to and separated from the rear end of said yarn introduction guide, (iii) a knotter for connecting the rear end of a continuous yarn formed by connecting a plurality of sample yarns to one another in an end-to-end manner, to the end of a fresh sample yarn introduced from said yarn introduction guide, and (iv) a yarn feed-out guide for guiding the continuous yarn in which said connecting operation has been completed, wherein when said suction pipe is separated from the rear end of said yarn introduction guide, it sucks and holds both the end of the sample yarn from the yarn introduction guide and the end of said continuous yarn through said yarn feed-out guide, (2) means for storing and feeding said continuous yarn, said storing and feeding means including a storing drum on which the continuous yarn is stored by introducing the continuous yarn from the peripheral direction of said drum and winding a predetermined qunatity of the continuous yarn on the drum and from which the stored continuous yarn is continuously taken out from the axial direction of the drum, the speed for winding the continuous yarn on the storing drum being higher than the speed for taking out the continuous yarn from said storing drum, and (3) a preset counter for indicating and counting a predetermined length of the continuous yarn stored in said storing and feeding means by one storing operation, wherein said preset counter transmits a signal when said storing and feeding means completes storing of the predetermined length of the continuous yarn, to instruct said storing and feeding means to stop the yarn storing operation and to instruct said sample yarn collecting means to prepare for the yarn connecting operation, and wherein said sample yarn collecting means transmits a signal on completion of the sample yarn collecting and connecting operation to cause said storing and feeding means to initiate the yarn storing operation.

8. An apparatus as set forth in claim 7 wherein means for reading the rotation number of the storing drum is disposed and a signal of the rotation number generated by said reading means is transmitted to said preset counter as the count signal.

9. An apparatus as set forth in claim 8 wherein at least one small magnet piece is attached to the side portion of the storing drum and a reed switch is disposed to face said small magnet piece, whereby the rotation number of the storing drum is counted.

10. An apparatus as set forth in claim 7 including means for counting the number of balloonings of the continuous yarn taken out from the storing drum to thereby inspect the quantity of the continuous yarn stored on the storing drum.

11. An apparatus as set forth in claim 7 wherein a plurality of yarn packages from which sample yarns are collected are hung on a hanging stand.

12. An apparatus as set forth in claim 7 wherein a plurality of yarn packages from which sample yarns are collected are arranged on an intermittently moving conveyor.

13. An apparatus as set forth in claim 7 wherein the yarn introduction guide has a cylindrical shape.

14. An apparatus as set forth in claim 7 wherein a sample yarn reserver having a suction opening is disposed adjacently to the yarn introduction guide.

15. An apparatus as set forth in claim 7 wherein a plurality of cylindrical yarn guids are disposed on the yarn introduction side of the yarn introduction guide, and cutter means capable of performing a yarn change-over operation among said cylindrical yarn guides is disposed between said yarn introduction guide and said cylindrical yarn guides.

16. An apparatus as set forth in claim 7 wherein means for reserving the continuous yarn is disposed between the knotter and the storing and feeding means.

17. An apparatus for preparing a continuous test yarn composed of end-to-end connected sample yarns having a certain length, comprising (1) a yarn introduction guide, the front end of which guides and introduces sample yarns, (2) a suction pipe which is movable so that the inlet of said pipe on the suction side is operated to be connected to and separated from the rear end of said yarn introduction guide, (3) a knotter for connecting the rear end of a continuous yarn formed by connecting a plurality of sample yarns to one another in an end-to-end manner, to the end of a fresh sample yarn introduced from said yarn introduction guide, and (4) a yarn feed-out guide for guiding the continuous yarn in which said connecting operation has been completed, wherein when said suction pipe is separated from the rear end of said yarn introduction guide, it sucks and holds both the end of the sample yarn from the yarn introduction guide and the end of said continuous yarn through said yarn feed-out guide.

18. An apparatus as set forth in claim 17 wherein a plurality of yarn packages from which sample yarns are collected are hung on a hanging stand.

19. An apparatus as set forth in claim 17 wherein a plurality of yarn packages from which sample yarns are collected are arranged on an intermittently moving conveyor.

20. An apparatus as set forth in claim 17 wherein the yarn introduction guide has a cylindrical shape.

21. An apparatus as set forth in claim 17 wherein a sample yarn reserver having a suction opening is disposed adjacently to the yarn introduction guide.

22. An apparatus as set forth in claim 17 wherein a a plurality of cylindrical yarn guides are disposed on the yarn introduction side of the yarn introduction guide, and cutter means capable of performing a yarn change-over operation among said cylindrical yarn guides is disposed between said yarn introduction guide and said cylindrical yarn guides.

23. An apparatus as set forth in claim 17 which further comprises a winder for winding the end-to-end connected continuous sample yarn in the form of a sample cheese.

24. An apparatus as set forth in claim 23 wherein means for reserving the continuous sample yarn is disposed between the knotter and the winder.

* * * * *